US011644582B2

(12) United States Patent
Ishii et al.

(10) Patent No.: US 11,644,582 B2
(45) Date of Patent: May 9, 2023

(54) RADIATION IMAGING APPARATUS COMPRISING A FIRST SCINTILLATOR PLATE, A SECOND SCINTILLATOR PLATE, AND AN IMAGING PORTION, AND RADIATION IMAGING SYSTEM

(71) Applicant: CANON KABUSHIKI KAISHA, Tokyo (JP)

(72) Inventors: Takamasa Ishii, Saitama (JP); Kosuke Terui, Kanagawa (JP); Kota Nishibe, Kanagawa (JP); Tomohiro Hoshina, Kanagawa (JP)

(73) Assignee: Canon Kabushiki Kaisha, Tokyo (JP)

( * ) Notice: Subject to any disclaimer, the term of this patent is extended or adjusted under 35 U.S.C. 154(b) by 23 days.

(21) Appl. No.: 17/084,199

(22) Filed: Oct. 29, 2020

(65) Prior Publication Data
US 2021/0132240 A1 May 6, 2021

(30) Foreign Application Priority Data
Nov. 5, 2019 (JP) .............................. JP2019-200885

(51) Int. Cl.
*A61B 6/00* (2006.01)
*G01T 1/20* (2006.01)

(52) U.S. Cl.
CPC ........ *G01T 1/20185* (2020.05); *A61B 6/4208* (2013.01); *A61B 6/4216* (2013.01); *A61B 6/4233* (2013.01); *A61B 6/4266* (2013.01); *A61B 6/52* (2013.01); *A61B 6/5205* (2013.01); *A61B 6/56* (2013.01); *A61B 6/563* (2013.01); *A61B 6/566* (2013.01); *G01T 1/2002* (2013.01); *G01T 1/2006* (2013.01);
(Continued)

(58) Field of Classification Search
CPC ....... A61B 6/42; A61B 6/4208; A61B 6/4233; A61B 6/4241; A61B 6/4266; A61B 6/52; A61B 6/5205; A61B 6/56; A61B 6/563; A61B 6/566; G01T 1/20; G01T 1/2002; G01T 1/2006; G01T 1/2008; G01T 1/2018; G01T 1/20182; G01T 1/20185; G01T 1/20186; G01T 1/20187; G01T 1/20188; G01T 1/20181
USPC .................... 378/5, 19, 98.8, 65; 250/370.09
See application file for complete search history.

(56) References Cited

U.S. PATENT DOCUMENTS 4,626,688 A * 12/1986 Barnes .................. A61B 6/032
250/361 R
4,870,667 A * 9/1989 Brunnett ................. G01T 1/202
378/19
(Continued)

FOREIGN PATENT DOCUMENTS

JP 2011158291 A 8/2011
JP 2016136094 A 7/2016

*Primary Examiner* — Allen C. Ho
(74) *Attorney, Agent, or Firm* — Canon U.S.A., Inc., IP Division

(57) ABSTRACT

A radiation imaging apparatus including: a first scintillator layer configured to convert a radiation (R) which has entered the first scintillator layer into light; a second scintillator layer configured to convert a radiation transmitted through the first scintillator layer into light; a fiber optic plate (FOP) provided between the first scintillator layer and the second scintillator layer; and an imaging portion configured to convert the light generated in the first scintillator layer and the light generated in the second scintillator layer into an electric signal.

9 Claims, 7 Drawing Sheets

(52) U.S. Cl.
CPC .......... *G01T 1/2008* (2013.01); *G01T 1/2018* (2013.01); *G01T 1/20181* (2020.05); *G01T 1/20182* (2020.05); *G01T 1/20186* (2020.05); *G01T 1/20187* (2020.05); *G01T 1/20188* (2020.05); *A61B 6/40* (2013.01)

(56) References Cited

U.S. PATENT DOCUMENTS

| | | | | |
|---|---|---|---|---|
| 4,945,242 A * | 7/1990 | Berger | ............ | H05G 1/60 250/370.06 |
| 4,945,243 A * | 7/1990 | Arques | ............ | H04N 5/374 250/370.06 |
| 5,514,874 A * | 5/1996 | Boone | ............ | G01T 1/20 250/486.1 |
| 5,594,253 A * | 1/1997 | Bueno | ............ | G01T 1/2018 250/367 |
| 5,864,146 A * | 1/1999 | Karellas | ............ | A61B 6/4258 378/191 |
| 6,535,574 B1 * | 3/2003 | Collins | ............ | A61N 5/1049 378/65 |
| 6,800,857 B2 * | 10/2004 | Kajiwara | ............ | G02B 6/08 250/370.11 |
| 7,266,176 B2 * | 9/2007 | Allison | ............ | A61N 5/1031 378/65 |
| 7,315,027 B2 * | 1/2008 | Okada | ............ | G01T 1/2018 250/370.11 |
| 7,388,208 B2 * | 6/2008 | Deych | ............ | G01T 1/2985 250/370.11 |
| 7,412,029 B2 * | 8/2008 | Myles | ............ | G16H 50/50 378/65 |
| 7,569,832 B2 * | 8/2009 | Tredwell | ............ | H01L 27/14632 250/370.11 |
| 7,671,342 B2 * | 3/2010 | Bani-Hashemi | ...... | G01T 1/2018 250/370.11 |
| 7,696,481 B2 * | 4/2010 | Tkaczyk | ............ | G01T 1/2985 250/363.02 |
| 7,834,321 B2 * | 11/2010 | Yorkston | ............ | G21K 4/00 250/370.09 |
| 7,929,665 B2 * | 4/2011 | Kang | ............ | G01T 1/2018 250/370.11 |
| 7,945,021 B2 * | 5/2011 | Shapiro | ............ | A61N 5/1048 378/65 |
| 8,338,789 B2 * | 12/2012 | Takihi | ............ | G01T 1/2008 250/366 |
| 8,442,184 B2 * | 5/2013 | Forthmann | ............ | A61B 6/032 378/5 |
| 8,648,312 B2 * | 2/2014 | Ichimura | ............ | G01T 1/202 250/367 |
| 8,729,478 B2 * | 5/2014 | Tredwell | ............ | G01T 1/2018 250/362 |
| 9,075,150 B2 * | 7/2015 | Tredwell | ............ | G01T 1/2018 |
| 9,182,504 B2 * | 11/2015 | Nishino | ............ | G01T 1/2012 |
| 9,316,750 B2 * | 4/2016 | Hosoi | ............ | G01T 1/2018 |
| 9,329,301 B2 * | 5/2016 | Suyama | ............ | G01V 5/005 |
| 9,372,269 B2 * | 6/2016 | Ho | ............ | G01T 1/2008 |
| 9,433,391 B2 * | 9/2016 | Miyazaki | ............ | G01T 1/248 |
| 9,588,232 B2 * | 3/2017 | Green | ............ | G01T 1/201 |
| 9,766,353 B2 * | 9/2017 | Kawanishi | ............ | G01T 1/2018 |
| 9,907,976 B2 * | 3/2018 | Bourke, Jr | ............ | A61N 5/062 |
| 10,490,593 B2 * | 11/2019 | Wu | ............ | H01L 27/14612 |
| 10,739,473 B2 * | 8/2020 | Baturin | ............ | G01T 1/2008 |
| 11,156,727 B2 * | 10/2021 | Shedlock | ............ | G01T 1/2018 |
| 11,340,359 B2 * | 5/2022 | Herrmann | ............ | A61B 6/032 |
| 11,346,962 B2 * | 5/2022 | Ullah | ............ | G01T 1/2008 |
| 11,460,590 B2 * | 10/2022 | Lubinsky | ............ | H01L 27/14663 |
| 2017/0097425 A1 * | 4/2017 | Shedlock | ............ | G01T 1/2002 |

* cited by examiner

RADIATION IMAGING APPARATUS COMPRISING A FIRST SCINTILLATOR PLATE, A SECOND SCINTILLATOR PLATE, AND AN IMAGING PORTION, AND RADIATION IMAGING SYSTEM

BACKGROUND

Field of the Disclosure

The present disclosure relates to a radiation imaging apparatus and a radiation imaging system which are configured to perform imaging using a radiation, and more particularly, to a radiation imaging apparatus and a radiation imaging system which are applicable to, for example, a medical image diagnosis apparatus and an analysis apparatus.

Description of the Related Art

A radiation imaging apparatus, in general, includes a scintillator (fluorescent substance) layer configured to convert a radiation entering the scintillator layer into light (for example, visible light) with a wavelength that can be detected by a photoelectric conversion element; and an imaging portion including the photoelectric conversion element configured to convert the light generated in the scintillator layer into an electric signal. To applying to medical image diagnosis, such radiation imaging apparatus having high sensitivity is desired in order to reduce radiation exposure of a patient. One example of methods for achieving the radiation imaging apparatus having high sensitivity is to increase a film thickness of the scintillator layer.

When the film thickness of the scintillator layer is increased, it is assumed that the light converted by the scintillator layer is scattered in the scintillator layer to thereby reduce sharpness of a radiation image. Thus, a scintillator used for the scintillator layer is desired to be a columnar crystal having high light directivity. Material for this type of scintillatorincludes CsI:Tl obtained by doping cesium iodide (CsI) with thallium (Tl). In addition, a structure having a fiber optic plate (FOP) is arranged between the imaging portion and the scintillator layer in order to ensure the sharpness of the radiation image while preventing radiation deterioration of the photoelectric conversion element. For example, in Japanese Patent Application Laid-Open No. 2011-158291, a scintillator plate with a scintillator of columnar crystals is formed on the FOP formed by bundling a plurality of optical fibers. Japanese Patent Application Laid-Open No. 2016-136094 describes a scintillator plate in which the FOP and the scintillator are bonded together.

In the scintillator plate disclosed in each of Japanese Patent Application Laid-Open No. 2011-158291 and Japanese Patent Application Laid-Open No. 2016-136094, the scintillator made of columnar crystals is used. Thus, light scattering in the scintillator layer is small. However, there is a gap, that is, an air layer, between a columnar crystal and a columnar crystal in the scintillator layer, and hence it is difficult to completely confine light in the columnar crystals. For this reason, even when the scintillator made of columnar crystals is used, a range of the light scattering in the scintillator layer becomes wider as the film thickness of the scintillator layer becomes larger. That is, the light converted by the scintillator layer having an increased film thickness is scattered in the scintillator layer before reaching the FOP, hence the sharpness of the radiation image is reduced even when the FOP has a function of causing the light to travel straight.

SUMMARY

The present disclosure provided in view of such a problem has an object to provide a mechanism for achieving a radiation imaging apparatus with high sensitivity and suppressing reduction in sharpness of a radiation image.

According to the present disclosure, a radiation imaging apparatus is provided. The radiation image apparatus includes a first scintillator layer configured to convert a radiation which has entered the first scintillator layer into light; a second scintillator layer configured to convert a radiation transmitted through the first scintillator layer into light; a fiber optic plate provided between the first scintillator layer and the second scintillator layer; and an imaging portion configured to convert the light generated in the first scintillator layer and the light generated in the second scintillator layer into an electric signal. The present disclosure also provides a radiation imaging system including the above-mentioned radiation imaging apparatus.

Further features of the present invention will become apparent from the following description of exemplary embodiments with reference to the attached drawings.

DESCRIPTION OF THE EMBODIMENTS

Modes for carrying out the present embodiments are described with reference to the drawings. In addition, when the radiation imaging apparatus is used for, for example, a medical image diagnosis apparatus and an analysis apparatus, light includes visible light and infrared light, and a radiation includes X-rays, alpha rays, beta rays, and gamma rays.

First Embodiment

Figure 1:
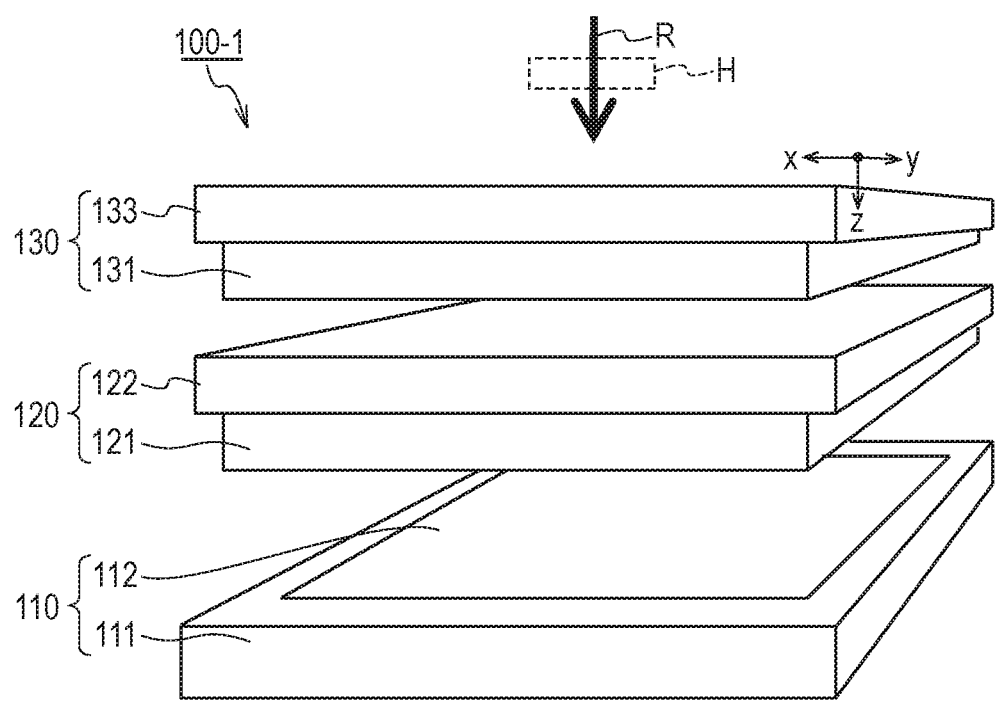
FIG. 1 is a perspective view for illustrating an example of a schematic configuration of a radiation imaging apparatus according to a first embodiment of the present invention.

FIG. 1 is a perspective view for illustrating an example of a schematic configuration of a radiation imaging apparatus 100 according to the first embodiment of the present invention. In FIG. 1, an xyz-coordinate system in which an incident direction of a radiation R is set as a z-direction and mutually perpendicular x-direciton and y-direction is perpendicular to the z-direction.

Figure 2:
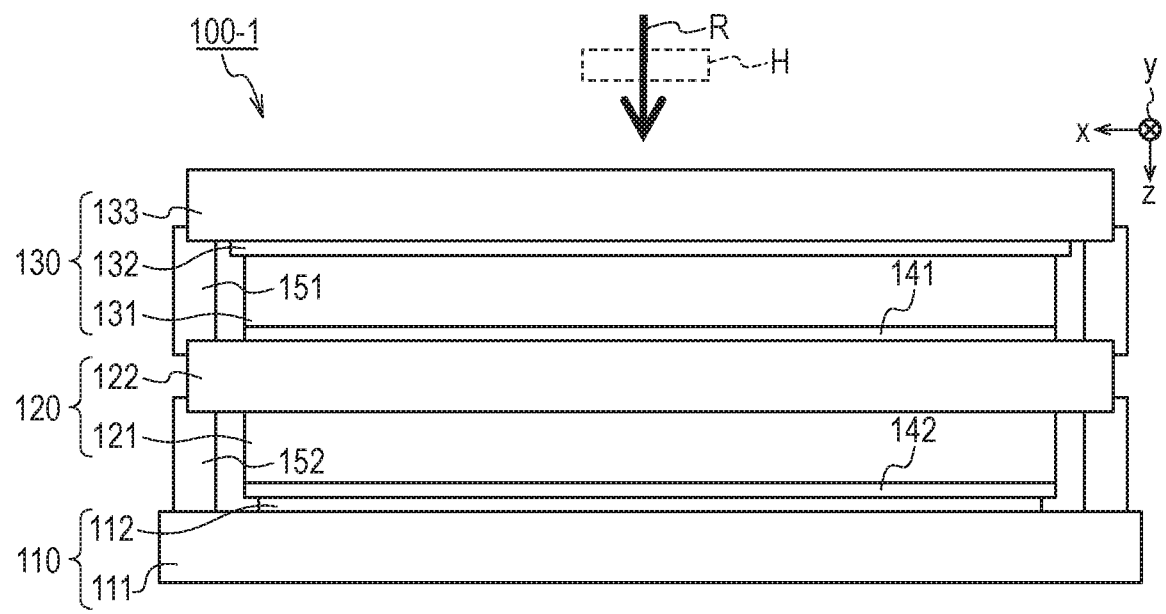
FIG. 2 is a cross-sectional view for illustrating an example of a detailed configuration of the radiation imaging apparatus according to the first embodiment of the present invention.

FIG. 2 is a cross-sectional view for illustrating an example of a detailed configuration of the radiation imaging apparatus 100 according to the first embodiment of the present invention. In FIG. 2, an xyz-coordinate system corresponding to the xyz-coordinate system illustrated in FIG. 1 is illustrated; and more specifically, FIG. 2 illustrates the detailed configuration of the radiation imaging apparatus 100 according to the first embodiment in a plane defined by the x-direction and the z-direction as illustrated in FIG. 1. In FIG. 2, the same components as those of the configuration illustrated in FIG. 1 are denoted by the same reference symbols.

In the following description of the first embodiment, the radiation imaging apparatus 100 according to the first embodiment illustrated in FIG. 1 and FIG. 2 is described as "radiation imaging apparatus 100-1".

As illustrated in FIG. 1 and FIG. 2, the radiation imaging apparatus 100-1 includes a first scintillator plate (first fluorescent substance plate) 130, a second scintillator plate (second fluorescent substance plate) 120, and an imaging portion 110. In addition, as illustrated in FIG. 2, the radiation imaging apparatus 100-1 further includes a first bonding member 141 and a second bonding member 142, and a first moisture resistant resin 151 and a second moisture resistant resin 152. In FIG. 1, the components are illustrated so as to be spaced apart from one another for the sake of description, but as illustrated in FIG. 2, those components are actually arranged by being stacked via the first bonding member 141 and the second bonding member 142.

As illustrated in FIG. 2, the first scintillator plate 130 includes a first scintillator layer 131, a reflective layer 132, and a support substrate 133.

The first scintillator layer 131 is a fluorescent substance configured to convert the radiation R entering the first scintillator layer 131 through the support substrate 133 and the reflective layer 132 (which includes the radiation R transmitted through an inspection object H) into light having a wavelength that can be detected by a photoelectric conversion element 112 of the imaging portion 110. The first scintillator layer 131 is made of, for example, CsI:Tl. In this case, for example, the first scintillator layer 131 is formed on the support substrate 133 provided with the reflective layer 132 by a vapor deposition method.

The reflective layer 132 illustrated in FIG. 2 is a layer for reflecting light, which is generated in the first scintillator layer 131 (which may include light generated in a second scintillator layer 121) to enter the reflective layer 132, in the z-direction so as to lead the light to the photoelectric conversion element 112 of the imaging portion 110. The reflective layer 132 is not always required in the first embodiment.

The support substrate 133 is a substrate arranged on a radiation incident side of the first scintillator layer 131 from which the radiation R enters, and configured to support the first scintillator layer 131. Examples of a material that can be used for the support substrate 133 include glass, amorphous carbon, CFRP, a resin film, aluminum, and titanium.

In this case, when the support substrate 133 is made of aluminum, titanium, or another material having a function of reflecting light, the reflective layer 132 is not always required. CsI:Tl has a deliquescent property, hence the first scintillator layer 131 made of CsI:Tl is desired to be covered with the support substrate 133 and a moisture proof protective film. Considering moisture proof, it is also desired to provide the first moisture resistant resin 151 in an outer peripheral portion of the radiation imaging apparatus 100. Specifically, the first moisture resistant resin 151 is provided between the support substrate 133 and a fiber optic plate (FOP) 122 of the second scintillator plate 120 and on the sides of the first scintillator layer 131. FIG. 2 illustrates and exemplary configuration in which the first scintillator layer 131 is in contact with the reflective layer 132. However, in order to protect the reflective layer 132 from CsI:Tl being a material for forming the first scintillator layer 131, an organic film may be further formed between the first scintillator layer 131 and the reflective layer 132.

As illustrated in FIG. 2, the second scintillator plate 120 is connected to the first scintillator plate 130 via the first bonding member 141, and is also connected to the imaging portion 110 via the second bonding member 142. As illustrated in FIG. 1 and FIG. 2, the second scintillator plate 120 includes a second scintillator layer 121 and a fiber optic plate (hereinafter referred to simply as "FOP") 122.

The second scintillator layer 121 is a fluorescent substance configured to convert the radiation R transmitted through the first scintillator plate 130 including the first scintillator layer 131 and the FOP 122. The radiation R transmitted through the inspection object H into light having a wavelength can be detected by the photoelectric conversion element 112 of the imaging portion 110. The second scintillator layer 121 is made of, for example, CsI:Tl. In this case, the second scintillator layer 121 is formed on the FOP 122 by, for example, the vapor deposition method. In addition, as described above, CsI:Tl has a deliquescent property, hence the second scintillator layer 121 made of CsI:Tl is desired to be covered with the FOP 122 and a moisture proof protective film (not shown). An organic film, for example, polyparaxylylene can be used as the moisture proof protective film. Considering moisture proof, it is also desired to provide the second moisture resistant resin 152 in the outer peripheral portion of the radiation imaging apparatus 100. Specifically, the second moisture resistant resin 152 is provided between the FOP 122 and an imaging substrate 111 of the imaging portion 110 and on the sides of the second scintillator layer 121. FIG. 2 illustrates a configuration example in which the second scintillator layer 121 is in contact with the FOP 122. However, in order to ensure adhesion strength or prevent the columnar crystals of the scintillator from being disturbed, an organic film may be formed between the second scintillator layer 121 and the FOP 122.

The FOP 122 may include a fiber optic plate by bundling a plurality of optical fibers between the first scintillator layer 131 and the second scintillator layer 121. As a numerical aperture NA of the FOP 122 is decreased, oblique light that enters the FOP 122 can be blocked. That is, the FOP 122 can limit an incident angle of incident light by the numerical aperture NA. In the currently embodiment, the FOP 122 may have a numerical aperture NA smaller than about 1.0. The FOP 122 also has a function of blocking the radiation R, and provides a greater shielding effect as the thickness becomes larger. The radiation imaging apparatus 100-1 according to the currently embodiment employs a mode in which the radiation R transmitting through the first scintillator layer 131 (without being absorbed by the first scintillator 131) is absorbed by the second scintillator layer 121 to be converted into light. Thus, in this embodiment, the FOP 122 may have a thickness of 1.0 mm or smaller. In this case, in consideration of a role of the FOP 122 serving as the supporting substrate of the second scintillator layer 121, the thickness of the FOP 122 may be set to 0.5 mm.

The imaging portion 110 converts the light generated in the first scintillator layer 131 and the light generated in the second scintillator layer 121 into an electric signal. As illustrated in FIG. 1 and FIG. 2, the imaging portion 110 includes the imaging substrate 111 and the photoelectric conversion element 112.

A plurality of photoelectric conversion elements 112 arranged in a matrix are formed on the imaging substrate 111. The photoelectric conversion element 112 detects incident light (light generated in the first scintillator layer 131 and light generated in the second scintillator layer 121) and converts the incident light into an electric signal. Examples of the photoelectric conversion element 112 that can be used include a PIN type sensor and an MIS type sensor that each use amorphous silicon.

It is possible to use a bonding member that may be melted or softened through heating for the first bending member 141 and the second bonding member 142. The first bonding member 141 and the second bonding member 142 are each formed of a sheet-like or liquid bonding material containing, for example, a styrene-based, olefin-based, vinyl chloride-based, urethane-based, or amide-based thermoplastic elastomer, which is also called "hot melt resin". For each of the first bonding member 141 and the second bonding member 142, it is also possible to use, for example, an acrylic-based or silicone-based adhesive sheet that has an adhesive function at room temperature.

In addition, considering moisture proof, the first moisture resistant resin 151 and the second moisture resistant resin 152 are provided in the outer peripheral portion of the radiation imaging apparatus 100. The first moisture resistant resin 151 and the second moisture resistant resin 152 can be made of, for example, a silicone resin, an acrylic resin, an epoxy resin, a urethane resin, or another resin.

As illustrated in FIG. 1 and FIG. 2, the radiation imaging apparatus 100-1 includes the support substrate 133, the first scintillator layer 131, the FOP 122, the second scintillator layer 121, and the imaging portion 110 arranged in the stated order from an incident side of the radiation R. In this case, the first scintillator layer 131 and the second scintillator layer 121 have different thicknesses.

The radiation R emitted for exposure toward the inspection object H in directions indicated by the arrows in FIG. 1 and FIG. 2 is attenuated by the inspection object H, and then enters the first scintillator layer 131 and the second scintillator layer 121. The first scintillator layer 131 and the second scintillator layer 121 each converts the incident radiation R into light having a wavelength that can be detected by the photoelectric conversion element 112 (for example, visible light). Then, the light converted by each of the first scintillator layer 131 and the second scintillator layer 121 enters the photoelectric conversion element 112 formed on the imaging substrate 111 to be converted into an electric signal, and a radiation image is generated based on this electric signal. Through repetition of this operation, the radiation imaging apparatus 100-1 can also obtain a moving image relating to the radiation image.

The sharpness of the radiation image is described as follows. In a case in where only one scintillator layer 131 is provided (the scintillator layer 121 is not provided) the radiation R transmitted through the inspection object H is converted into visible light by the scintillator layer 131. When the converted light is caused to travel straight to the photoelectric conversion element 112, a radiation image having high sharpness may be obtained. CsI:Tl forming the scintillator layer 131 is a columnar crystal; and thus has high light directivity with the small light scattering in the scintillator layer 131. However, a gap in the form of an air layer between a columnar crystal and a columnar crystal with this gap being an air layer makes it is difficult to completely confine light in the columnar crystals. Thus, the light converted in the vicinity of a surface of the scintillator layer 131 from which the radiation R enters diffusely travels toward a surface of the scintillator layer 131 from which the light exits, which is positioned on the photoelectric conversion element 112 side, while being repeatedly scattered. Meanwhile, a part of the light converted in the vicinity of the surface of the scintillator layer 131 from which the light exits diffusely travels, while being repeatedly scattered, toward the surface side of the scintillator layer 131 from which the radiation R enters, and is reflected by the reflective layer 132 to return, while being further diffused, to the exit surface of the scintillator layer 131. As the thickness of the scintillator layer 131 becomes larger, a range of the light diffusion becomes wider. Thus, even when the FOP 122 is used, as the thickness of the scintillator layer 131 becomes larger, a ratio of diffused light included in the light entering the FOP 122 increases, and the sharpness of the radiation image decreases.

In view of this, in the first embodiment, as the scintillator layers, the two scintillator layers of the first scintillator layer 131 and the second scintillator layer 121, are provided with the FOP 122 being interposed therebetween. In the first embodiment, the two scintillator layers are provided in this manner, and hence it is possible to set the thickness of each of the first scintillator layer 131 and the second scintillator layer 121 so that the total thickness of the thickness of the first scintillator layer 131 and the thickness of the second scintillator layer 121 is equal to or larger than a thickness of one scintillator layer which has hitherto been required. Each of the first scintillator layer 131 and the second scintillator layer 121 can be made smaller in thickness (thinner) than the thickness of one scintillator layer which has hitherto been required, and hence it is possible to reduce the range of the light diffusion within each of the first scintillator layer 131 and the second scintillator layer 121. The thicknesses of the first scintillator layer 131 and the second scintillator layer 121 may be set unequal (may be set different) to each other. In this case, the first scintillator layer 131 positioned at the incident side of the radiation R mainly converts the low-energy radiation R into light, and the second scintillator layer 121 positioned at the photoelectric conversion element 112 side mainly converts the high-energy radiation R transmitting through the first scintillator layer 131 and the FOP 122 into light. Thus, it is desired to determine the thickness of each of the first scintillator layer 131 and the second scintillator layer 121 depending on the properties of the radiation R to be used.

Now, the sharpness of the radiation image is described in more detail as follows. The radiation R absorbed by the first scintillator layer 131 is converted into light entering the second scintillator layer 121 through the FOP 122. The first scintillator layer 131 has a thickness smaller (thinner) than the thickness of the scintillator in the single-scintillator-layer structure, hence the ratio of diffused light included in the light entering the FOP 122 is small. In addition, some of the light converted by the first scintillator layer 131 travels toward the reflective layer 132. This light is reflected by the reflective layer 132 to enter the FOP 122, but the diffusion range is smaller as the first scintillator layer 131 is small in thickness (thin). That is, the light transmitting through the FOP 122 to enter the second scintillator layer 121 has high sharpness. As the radiation R that has not been absorbed by the first scintillator layer 131 transmits through the FOP 122 to enter the second scintillator layer 121. This radiation R is converted into light by the second scintillator layer 121 entering the photoelectric conversion element 112. The second scintillator layer 121 is also smaller in thickness (thinner) than the thickness of the scintillator layer in the single-scintillator-layer structure, hence the ratio of diffused light included in the light entering the photoelectric conversion element 112 is small. In addition, some of the light converted by the second scintillator layer 121 travels toward the FOP 122. A part of this light is reflected by the FOP 122 to enter the photoelectric conversion element 112. As the second scintillator layer 121 is small in thickness (thin), the diffusion range is small. In addition, a part of the light entering the FOP 122 is reflected by the reflective layer 132 through the first scintillator layer 131 to return along the same path as described above.

As described above, in the radiation imaging apparatus 100-1 two scintillator layers of the first scintillator layer 131 and the second scintillator layer 121 are provided with the FOP 122 being interposed therebetween. Each of the first scintillator layer 131 and the second scintillator layer 121 can be made smaller in thickness (thinner) than the thickness of the single scintillator layer. With this, it is possible to achieve the radiation imaging apparatus having high sensitivity by setting the total thickness of the thickness of the first scintillator layer 131 and the thickness of the second scintillator layer 121 to be equal to or larger than a predetermined thickness, and it is also possible to reduce the range of the light diffusion within each of the first scintillator layer 131 and the second scintillator layer 121 and reduce the ratio of diffused light included in the light entering the photoelectric conversion element 112, to thereby be able to suppress reduction in sharpness of the radiation image.

Further, the FOP 122 having a numerical aperture NA smaller than 1.0 is arranged between the first scintillator layer 131 and the second scintillator layer 121, hence it is possible to limit incident angles of light entering both surfaces of an upper surface and a lower surface of the FOP 122. That is, it is possible to correct the diffused light close to that of straight traveling light halfway through a scintillator layer group of the first scintillator layer 131 and the second scintillator layer 121 by arranging the FOP 122 between the first scintillator layer 131 and the second scintillator layer 121.

Second Embodiment

In the following description of the second embodiment, description of matters common to the first embodiment described above is omitted, and matters different from those of the first embodiment described above are described.

Figure 3:
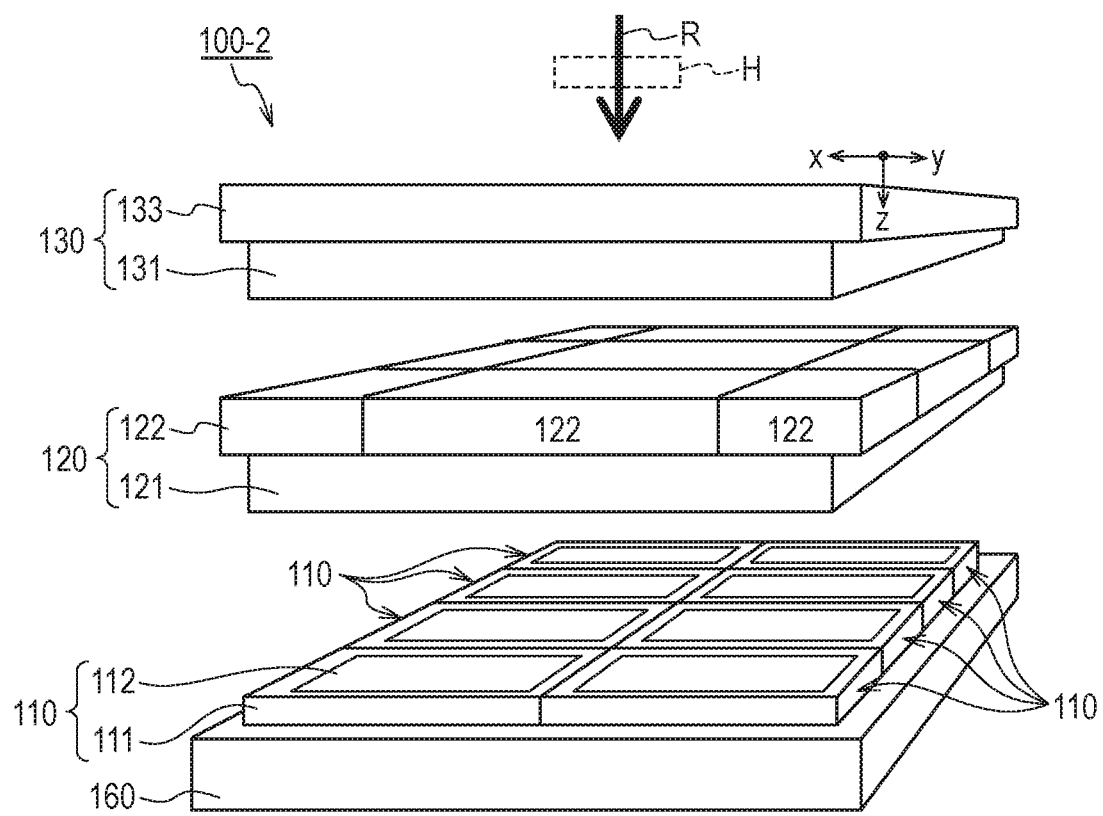
FIG. 3 is a perspective view for illustrating an example of a schematic configuration of a radiation imaging apparatus according to a second embodiment of the present invention.

FIG. 3 is a perspective view for illustrating an example of a schematic configuration of the radiation imaging apparatus 100 according to the second embodiment. In FIG. 3, an xyz-coordinate system corresponding to the xyz-coordinate system illustrated in FIG. 1 and FIG. 2 is illustrated. Further, in FIG. 3, the same components as those of the configuration illustrated in FIG. 1 and FIG. 2 are denoted by the same reference symbols, and detailed description thereof is omitted.

Figure 4:
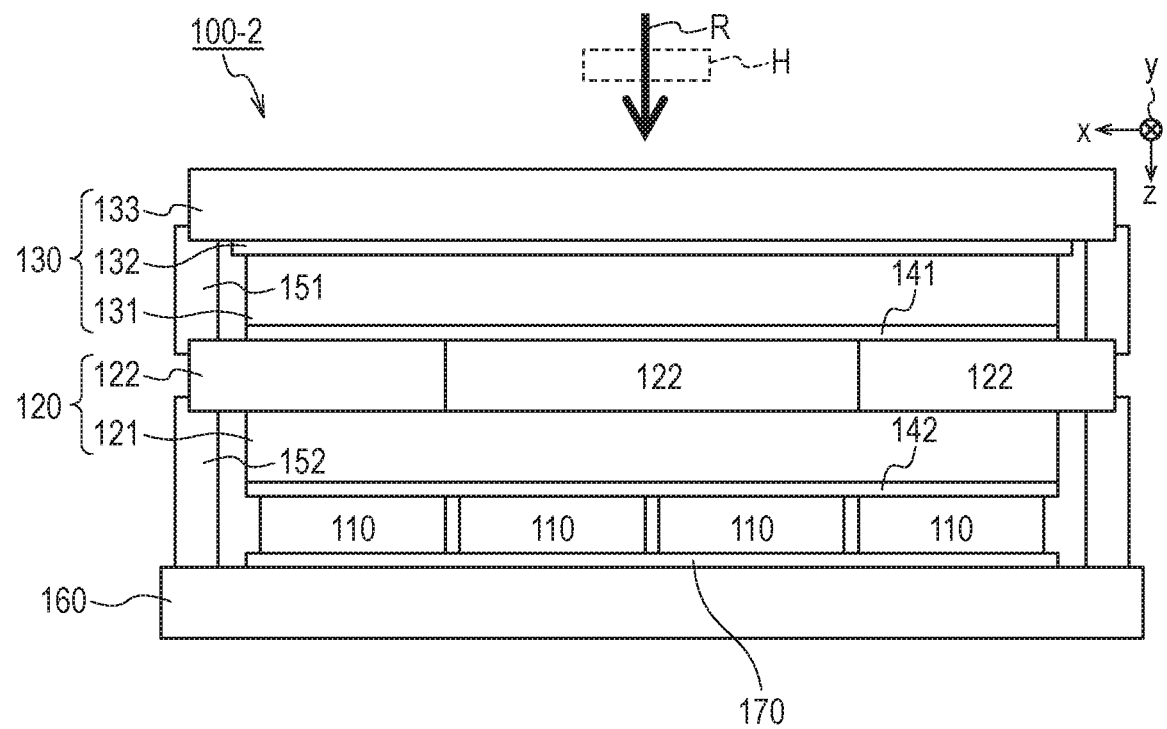
FIG. 4 is a cross-sectional view for illustrating an example of a detailed configuration of the radiation imaging apparatus according to the second embodiment of the present invention.

FIG. 4 is a cross-sectional view for illustrating an example of a detailed configuration of the radiation imaging apparatus 100 according to the second embodiment. In FIG. 4, an xyz-coordinate system corresponding to the xyz-coordinate system illustrated in FIG. 3 is illustrated, and more specifically, FIG. 4 is an illustration of the detailed configuration of the radiation imaging apparatus 100 according to the second embodiment in a plane defined by the x-direction and the z-direction illustrated in FIG. 3. In FIG. 4, the same components as those of the configuration illustrated in FIG. 3 are denoted by the same reference symbols.

In the following description of the second embodiment, the radiation imaging apparatus 100 illustrated in FIG. 3 and FIG. 4 is described as "radiation imaging apparatus 100-2". Differences from the first embodiment described above are described below.

As illustrated in FIG. 3 and FIG. 4, the radiation imaging apparatus 100-2 includes the first scintillator plate 130, the second scintillator plate 120, the imaging portions 110, and a fixing substrate 160. In addition, as illustrated in FIG. 4, the radiation imaging apparatus 100-2 further includes the first bonding member 141 and the second bonding member 142, the first moisture resistant resin 151 and the second moisture resistant resin 152, and a fixing member 170. In FIG. 3, the components are illustrated so as to be spaced apart from one another for the sake of description, but as illustrated in FIG. 4, those components are actually arranged by being stacked via the first bonding member 141, the second bonding member 142, and the fixing member 170.

As illustrated in FIG. 3 and FIG. 4, the radiation imaging apparatus 100-2 includes a plurality of imaging portions 110. Each imaging portion 110 includes one of a plurality of photoelectric conversion elements 112 arranged on the imaging substrate 111 in a matrix, and is configured to detect the light generated in the first scintillator layer 131 and the light generated in the second scintillator layer 121 to convert the light into an electric signal. As the photoelectric conversion element 112, for example, a CMOS sensor using crystalline silicon can be used.

The plurality of imaging portions 110 are fixed to the fixing substrate 160 via the fixing member 170. In the CMOS sensor applied as the photoelectric conversion element 112, the size of a crystalline silicon wafer is limited, hence a desired large-sized imaging substrate may not be able to be manufactured through use of a single imaging substrate 111. In view of this, as illustrated in FIG. 3, unlike in the first embodiment, the imaging portions 110 including the imaging substrates 111 are formed by being arranged in a 2×4 matrix. However, the number of arrayed imaging substrates 111 is not limited to this 2×4 matrix array.

Examples of a material that can be used for the fixing substrate 160 include glass, amorphous carbon, CFRP, and aluminum.

For the fixing member 170, it is possible to use, for example, a sheet-like bonding material obtained by arranging bonding layers above and below a foamed body having voids. This kind of bonding material has large elasticity due to the voids in the foamed body, and is thus effective in absorbing variations in height of the plurality of imaging substrates 111 and flattening an imaging surface. It is also possible to use, for example, a sheet-like or liquid bonding material containing, for example, a silicone resin, an acrylic resin, an epoxy resin, a urethane resin, or a hot melt resin.

In addition, as illustrated in FIG. 3 and FIG. 4, the second scintillator plate 120 includes the second scintillator layer 121 and a plurality of FOPs 122. Each FOP 122 is configured by bundling a plurality of optical fibers, hence a desired large-sized FOP may not be able to be manufactured through use of one FOP 122. In view of this, as illustrated in FIG. 3, a mode in which the FOPs 122 are arranged in a 3×3 matrix is adopted. However, the number of arrayed FOPs 122 is not limited to this 3×3 matrix array.

The radiation imaging apparatus 100-2 also includes the two scintillator layers of the first scintillator layer 131 and the second scintillator layer 121 with the FOPs 122 being interposed therebetween, hence the same effects as those of the first embodiment described above can be produced. That is, with the radiation imaging apparatus 100-2, it is possible to achieve the radiation imaging apparatus having high sensitivity and also reduce the ratio of diffused light included in the light entering the photoelectric conversion element 112, to thereby be able to suppress the reduction in sharpness of the radiation image.

Third Embodiment

Next, a third embodiment is described. In the following description of the third embodiment, description of matters common to the first and second embodiments described above is omitted, and matters different from those of the first and second embodiments described above are described.

Figure 5:
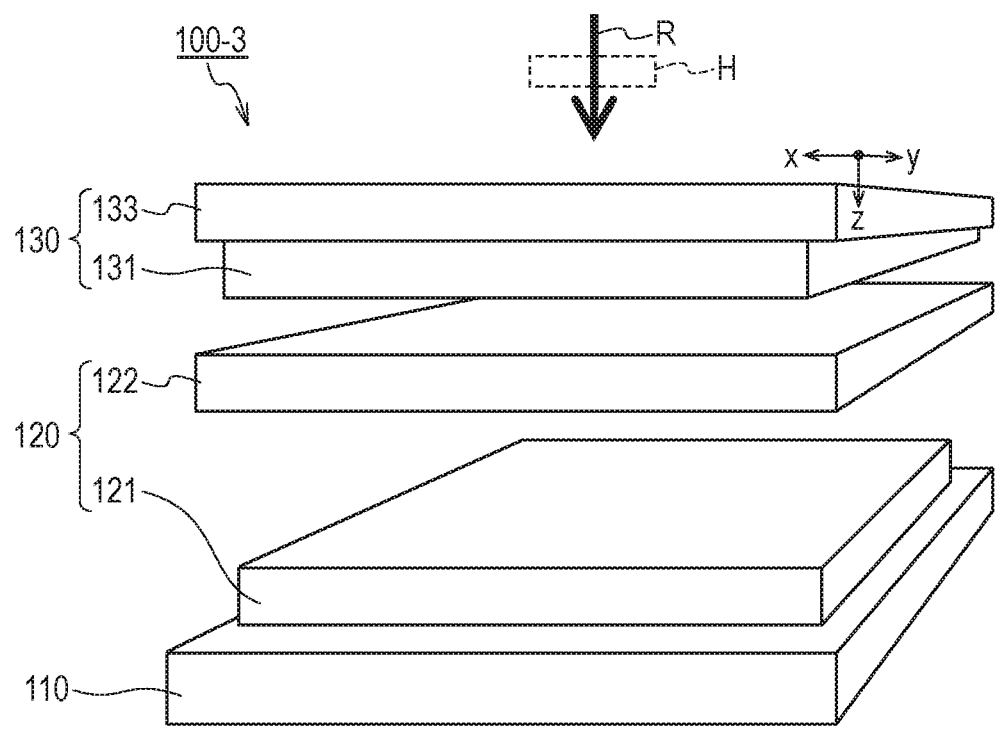
FIG. 5 is a perspective view for illustrating an example of a schematic configuration of a radiation imaging apparatus according to a third embodiment of the present invention.

FIG. 5 is a perspective view for illustrating an example of a schematic configuration of the radiation imaging apparatus 100 according to the third embodiment of the present invention. In FIG. 5, an xyz-coordinate system corresponding to the xyz-coordinate system illustrated in FIG. 1 and FIG. 2 is illustrated. Further, in FIG. 5, the same components as those of the configuration illustrated in FIG. 1 and FIG. 2 are denoted by the same reference symbols, and detailed description thereof is omitted.

Figure 6:
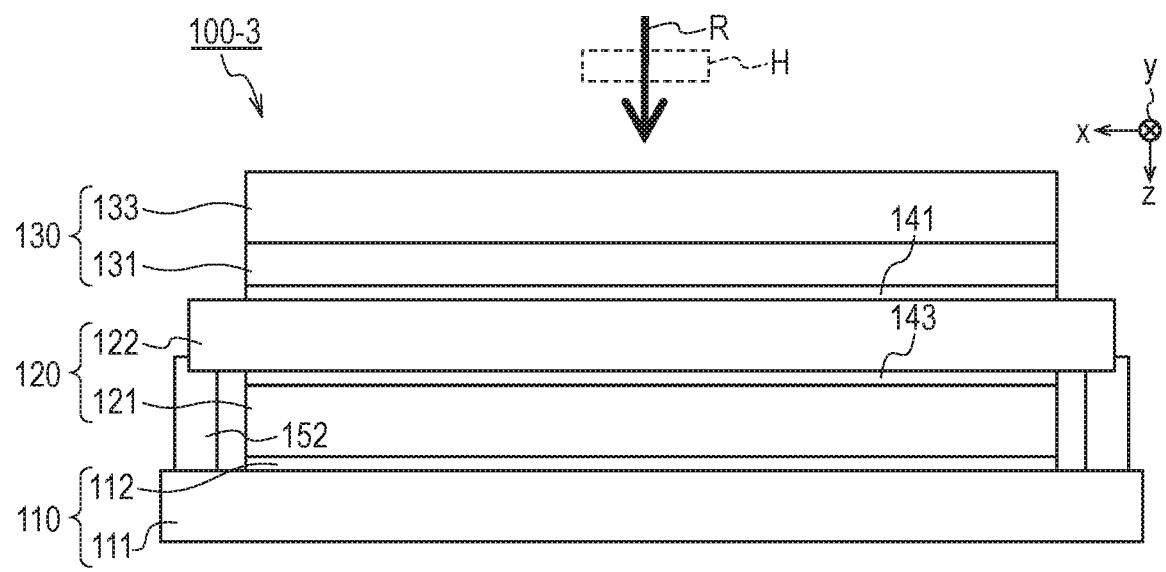
FIG. 6 is a cross-sectional view for illustrating an example of a detailed configuration of the radiation imaging apparatus according to the third embodiment of the present invention.

FIG. 6 is a cross-sectional view for illustrating an example of a detailed configuration of the radiation imaging apparatus 100 according to the third embodiment of the present invention. In FIG. 6, an xyz-coordinate system corresponding to the xyz-coordinate system illustrated in FIG. 5 is illustrated, and more specifically, FIG. 6 is an illustration of the detailed configuration of the radiation imaging apparatus 100 in a plane defined by x-direction and z-direction illustrated in FIG. 5. In FIG. 6, the same components as those of the configuration illustrated in FIG. 5 are denoted by the same reference symbols.

In the following description of the third embodiment, the radiation imaging apparatus 100 illustrated in FIG. 5 and FIG. 6 is described as "radiation imaging apparatus 100-3". Differences from the first and second embodiments described above are described below.

As illustrated in FIG. 5 and FIG. 6, the radiation imaging apparatus 100-3 includes the first scintillator plate 130, the second scintillator plate 120, and the imaging portion 110. In addition, as illustrated in FIG. 6, the radiation imaging apparatus 100-3 further includes the first bonding member 141, a third bonding member 143, and the second moisture resistant resin 152. In FIG. 5, the components are illustrated so as to be spaced apart from one another for the sake of description, but as illustrated in FIG. 6, those components may be arranged by being stacked via the first bonding member 141 and the third bonding member 143.

The second scintillator layer 121 is made of, for example, CsI:Tl. In this case, the second scintillator layer 121 is formed on the imaging substrate 111 by the vapor deposition method. In addition, as described above, CsI:Tl has a deliquescent property, hence the second scintillator layer 121 made of CsI:Tl is desired to be covered with the imaging substrate 111 and a moisture proof protective film (not shown). The moisture proof protective film formed on the second scintillator layer 121 or the second scintillator layer 121 may be connected to the FOP 122 via the third bonding member 143.

As illustrated in FIG. 6, the first scintillator plate 130 includes the first scintillator layer 131 and the support substrate 133. FIG. 6 illustrates an example in which a component corresponding to the reflective layer 132 illustrated in FIG. 2 is not provided. The first scintillator plate 130 is a non-columnar scintillator plate in which a resin and a granular $Gd_2O_2S$ (GOS) fluorescent substance forming the first scintillator layer 131 are formed on the support substrate 133 by a coating method. In the current embodiment, the support substrate 133 is desired to be made of a material having a function of reflecting light. For the support substrate 133, not only a metal material, but also, for example, a PET resin plate containing titanium oxide ($TiO_2$) particles may be used. The GOS forming the first scintillator layer 131 also exhibits less deterioration due to humidity with the resin being arranged around the GOS particles, hence the first moisture resistant resin 151 is not arranged in FIG. 6. The non-columnar scintillator plate may be manufactured by the coating method, and hence the production cost may be reduced in some cases. The GOS forming the first scintillator layer 131 is granular, hence the light scattering and diffusion in the scintillator layer are larger than those in the columnar CsI:Tl. However, it is possible to reduce the thickness of the first scintillator layer 131 made of GOS by arranging the second scintillator layer 121 made of CsI:Tl at the side of the imaging substrate 111 and increasing the thickness of the second scintillator layer 121. That is, the first scintillator layer 131 is smaller in thickness (thinner) than the thickness of the second scintillator layer 121. It is also possible to correct the diffused light of the first scintillator layer 131 close to that of straight traveling light by arranging the FOP 122 between the first scintillator layer 131 and the second scintillator layer 121.

The radiation imaging apparatus 100-3 may also include the two scintillator layers of the first scintillator layer 131 and the second scintillator layer 121 with the FOP 122 being interposed therebetween, hence the same effects as those of the first embodiment described above can be produced. That is, with the radiation imaging apparatus 100-3 according to the current embodiment, it is possible to achieve the radiation imaging apparatus having high sensitivity and also reduce the ratio of diffused light included in the light entering the photoelectric conversion element 112, to thereby be able to suppress the reduction in sharpness of the radiation image.

Fourth Embodiment

Next, a fourth embodiment is described. In the following description of the fourth embodiment, description of matters common to the first to third embodiments described above is omitted, and matters different from those of the first to third embodiments described above are described.

Figure 7:
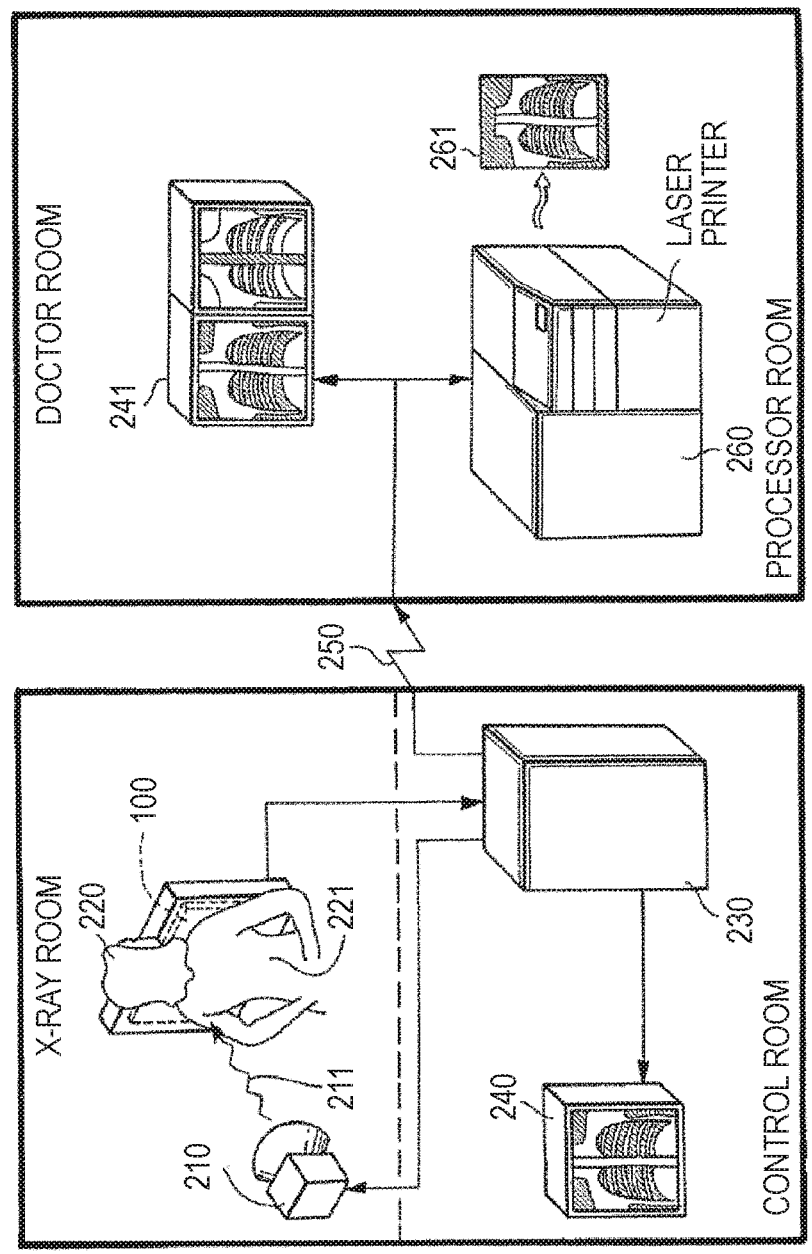
FIG. 7 is a conceptual diagram of an X-ray imaging system (radiation imaging system) according to a fourth embodiment of the present invention, which uses the radiation imaging apparatus according to any one of the first to third embodiments.

FIG. 7 is a conceptual diagram of an X-ray imaging system (radiation imaging system) according to the fourth embodiment, which uses the radiation imaging apparatus 100 according to any one of the first to third embodiments.

X-rays 211 being the radiation R generated by an X-ray tube 210 (radiation generation unit) are transmitted through a chest 221 of a person 220 to be inspected, for example, the inspection object H, to enter the radiation imaging apparatus 100 according to any one of the first to third embodiments. The X-rays 211 that have entered this radiation imaging apparatus 100 include information on the inside of the body of the person 220 to be inspected.

In the radiation imaging apparatus 100, the first scintillator layer 131 and the second scintillator layer 121 emit light in response to the X-rays 211 that have entered the radiation imaging apparatus 100. The light generated in those scintillator layers is photoelectrically converted into an electric signal by the imaging portion 110 to thereby obtain electrical information on the inside of the body of the person 220 to be inspected. This electrical information is converted into a digital signal and image-processed by an image processor 230 serving as a signal processing unit, and thus can be observed on a display 240 serving as a display unit of a control room.

Further, the electrical information obtained by the radiation imaging apparatus 100 and processed by the image processor 230 can be transferred to a remote site by a transmission unit 250, for example, a telephone line, and can be transmitted to, for example, a doctor room located at another place. In the doctor room located at another place, the electrical information received via the transmission unit 250 can be displayed on a display 241 serving as the display unit or can be stored in a recording unit, for example, an optical disc, and hence a doctor in the remote site can also perform diagnosis. The electrical information can also be recorded on a film 261 serving as a recording medium by a film processor 260 serving as a recording unit.

All the embodiments described above merely describe embodied examples for carrying out the present invention. Therefore, the technical scope of the present invention should not be read as restrictive by the embodiments described above. Specifically, the present invention can be carried out in various forms without departing from the technical ideas or main features of the present invention.

It is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2019-200885, filed Nov. 5, 2019, which is hereby incorporated by reference herein in its entirety.

What is claimed is:

1. A radiation imaging apparatus comprising:
    a first scintillator layer configured to convert a radiation having entered the first scintillator layer into light;
    a second scintillator layer configured to convert a radiation transmitting through the first scintillator layer into light;
    a fiber optic plate provided between the first scintillator layer and the second scintillator layer; and
    an imaging portion configured to convert the light generated in the first scintillator layer and the light generated in the second scintillator layer into an electric signal,
    wherein the first scintillator layer, the fiber optic plate, the second scintillator layer, and the imaging portion are arranged in sequence from an incident side of the radiation.

2. The radiation imaging apparatus according to claim 1, wherein the fiber optic plate has a numerical aperture NA smaller than 1.0.

3. The radiation imaging apparatus according to claim 1, wherein the fiber optic plate has a thickness of 1.0 mm or smaller.

4. The radiation imaging apparatus according to claim 1, wherein each of the first scintillator layer and the second scintillator layer comprises CsI:Tl.

5. The radiation imaging apparatus according to claim 1, wherein the first scintillator layer comprises GOS, and wherein the second scintillator layer comprises CsI:Tl.

6. The radiation imaging apparatus according to claim 1, wherein the first scintillator layer and the second scintillator layer are different in thickness.

7. A radiation imaging apparatus further comprising:
    a first scintillator layer configured to convert a radiation having entered the first scintillator layer into light;
    a first scintillator layer configured to convert a radiation having entered the first scintillator layer into light;
    a second scintillator layer configured to convert a radiation transmitting through the first scintillator layer into light;
    a fiber optic plate provided between the first scintillator layer and the second scintillator layer;
    an imaging portion configured to convert the light generated in the first scintillator layer and the light generated in the second scintillator layer into an electric signal; and
    a moisture resistant resin between the fiber optic plate and the imaging portion and on sides of the second scintillator layer.

8. A radiation imaging apparatus further comprising:
    a first scintillator layer configured to convert a radiation having entered the first scintillator layer into light;
    a second scintillator layer configured to convert a radiation transmitting through the first scintillator layer into light;
    a fiber optic plate provided between the first scintillator layer and the second scintillator layer;
    an imaging portion configured to convert the light generated in the first scintillator layer and the light generated in the second scintillator layer into an electric signal;
    a support substrate configured to support the first scintillator layer at an incident side of the radiation of the first scintillator layer;
    a first moisture resistant resin between the support substrate and the fiber optic plate, and on sides of the first scintillator layer; and
    a second moisture resistant resin between the fiber optic plate and the imaging portion, and on sides of the second scintillator layer.

9. A radiation imaging system comprising:
    a radiation imaging apparatus of claim 1;
    a signal processing unit configured to process the electric signal obtained by the imaging portion;
    a recording unit configured to record the electric signal processed by the signal processing unit;
    a display unit configured to display the electric signal processed by the signal processing unit;
    a transmission unit configured to transmit the electric signal processed by the signal processing unit; and
    a radiation generation unit configured to generate the radiation.

* * * * *